United States Patent [19]

Shi-jie

[11] Patent Number: 4,868,207
[45] Date of Patent: Sep. 19, 1989

[54] BIS (METHYLENEDIOXY) BIPHENYL COMPOUNDS USEFUL FOR THE TREATMENT OF LIVER DISEASES

[75] Inventor: Gu Shi-jie, Beijing, China

[73] Assignees: Taisho Pharmaceutical Co., Ltd., Japan; The Institute of Material Mederia Medica of Chinese Academy of Medical Sciences, China

[21] Appl. No.: 225,365

[22] Filed: Jul. 28, 1988

[51] Int. Cl.$^4$ .................. A61K 31/335; C07D 317/64
[52] U.S. Cl. .................................... 514/464; 549/435
[58] Field of Search ......................... 549/435; 514/464

[56] References Cited

FOREIGN PATENT DOCUMENTS 60-209582 10/1985 Japan .
87/272 12/1987 PCT Int'l Appl. .

OTHER PUBLICATIONS

Weygand/Hilgetag, Preparative Organic Chemistry, ed. Hilgeteg Huertin, John Wiley & Sons, New York, 1972, p. 375.

Primary Examiner—Nicky Chan
Attorney, Agent, or Firm—Lorusso & Loud

[57] ABSTRACT

Bis(methylenedioxy)biphenyl compounds represented by the formula

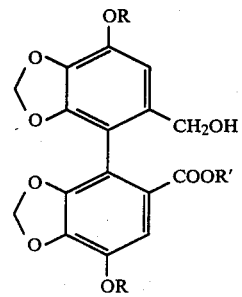

wherein R is an alkyl group having 1 to 6 carbon atoms or a phenyl group, and R' is a hydrogen atom or an alkyl group having 1 to 6 carbon atoms, are disclosed. These compounds are useful as therapeutic agents for liver diseases.

2 Claims, No Drawings

BIS (METHYLENEDIOXY) BIPHENYL COMPOUNDS USEFUL FOR THE TREATMENT OF LIVER DISEASES

BACKGROUND OF THE INVENTION

1. Field of the Invention

The present invention relates to bis(methylenedioxy)-biphenyl compounds, and more specifically to 2,3,2',3'-bis(methylenedioxy)biphenyl compounds useful as the therapeutic agents for liver diseases.

2. Description of the Prior Art

In the past, dialkyl 4,4'-dialkoxy-5,6,5',6'-dimethylenedioxybiphenyl-2,2'-dicarboxylates have been known to be useful as the therapeutic agent for chronic hepatitis and hepatic circhosis derived from hepatitis (Japanese Patent Laid-Open No. 60-209582). However, 2,3,2',3'-bis(methylenedioxy)biphenyl compounds having an alkoxycarbonyl group or carboxyl group at the 6-position and hydroxymethyl group at the 6'-position are not yet known. By the way, there is a need of compounds having a desirable effect without side effects as the therapeutic agents for chronic hepatitis and hepatic circhosis, for example, compounds capable of activating drug metabolism enzyme in liver and having a potent protective effect against hepatotoxicity.

SUMMARY OF THE INVENTION

As a result of the earnest researches to develop improved therapeutic agents for liver diseases, the present inventor has found that 2,3,2',3'-bis(methylenedioxy)-biphenyl compounds having an alkoxycarbonyl group or a carboxyl group at the 6-position and hydroxymethyl group at the 6'-position exhibit a potent protective effect against hepatotoxicity induced by carbon tetrachloride, thioacetoamide and acetoaminophen as well as an effect to activate drug metabolism enzyme in liver, and are extremely useful as the therapeutic agents for liver diseases. The present invention is based on the findings.

An object of the present invention is to provide bis(-methylenedioxy)biphenyl compounds represented by the formula

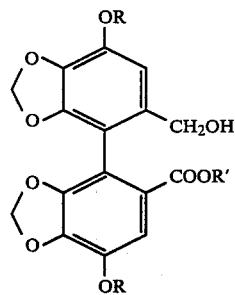

I wherein R is an alkyl group having 1 to 6 carbon atoms or a phenyl group, and R' is a hydrogen atom or an alkyl group having 1 to 6 carbon atoms.

Another object of the present invention is to provide a method for preparing bis(methylenedioxy)biphenyl compounds of Formula I which comprises reacting a compound represented by the formula

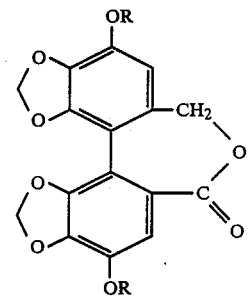

V wherein R is as defined above, with an alcohol of R"OH (wherein R" is R' other than hydrogen atom), or further hydrolyzing the resulting compound.

Still another object of the present invention is to provide a pharmaceutical composition for the treatment of liver diseases which comprises a bis(methylenedioxy)biphenyl compound of Formula I as an active ingredient, together with a pharmaceutically acceptable carrier or diluent.

DETAILED DESCRIPTION OF THE INVENTION

In the present invention, the alkyl group having 1 to 6 carbon atoms for R and R' may be a straight or branched chain alkyl group such as, for example, a methyl group, an ethyl group, a propyl group, an iso-propyl group, a butyl group, an iso-butyl group, a pentyl group, a hexyl group and the like, but is preferably an alkyl group having 1 to 4 carbon atoms.

The bis(methylenedioxy)biphenyl compounds of the present invention can be prepared by the method indicated in the following reaction scheme wherein R and R" are as defined above.

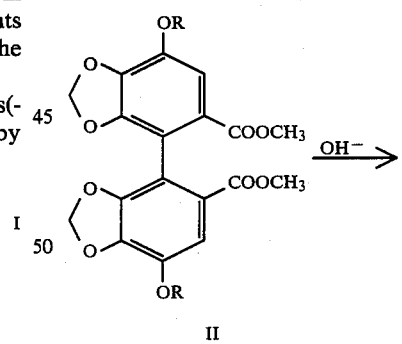

II

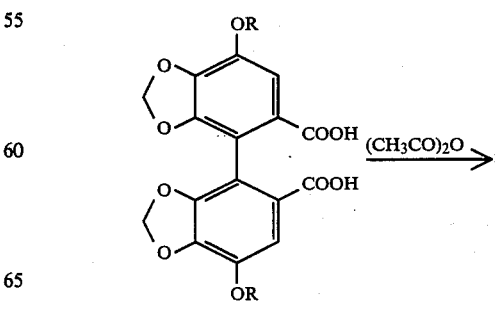

III

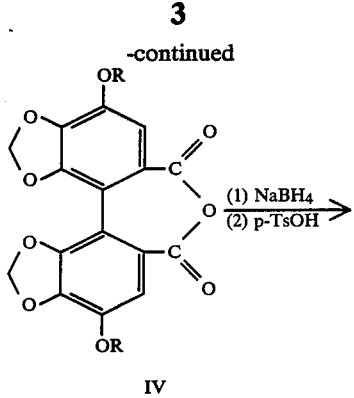

IV

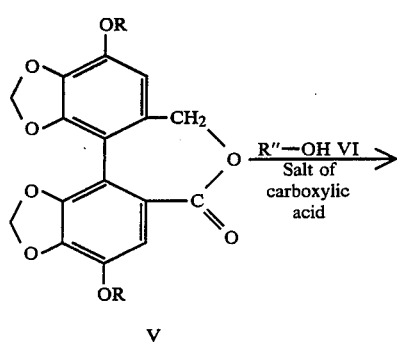

V

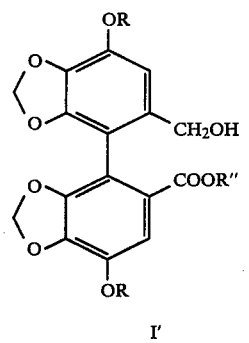

I'

In the reaction scheme, the known compound of Formula II (prepared by a method described in Japanese Patent Laid-Open No. 60-209582 or the analogs thereof) is hydrolyzed according to the ordinary hydrolysis of esters using alkali hydroxide (sodium hydroxide, potassium hydroxide and the like) to give a carboxylic acid of Formula III. Then, this compound and acetic anhydride are heated together to give an anhydride of Formula IV, which is then reduced with sodium borohydride, followed by heating with p-toluenesulfonic acid, and a lactone of Formula V is obtained. The lactone of Formula V is reacted with an alcohol of Formula VI in the presence of a salt of a carboxylic acid to give the compound of Formula I'. Preferable examples of the salt of the carboxylic acid are sodium or potassium salt of an aliphatic saturated monocarboxylic acid having 2 to 7 carbon atoms, such as sodium acetate, potassium acetate, sodium propionate, potassium propionate, sodium valerate, potassium valerate and the like. Examples of the alcohol of Formula VI are an alcohol having 1 to 6 carbon atoms such as methanol, ethanol, propanol, iso-propanol, butanol, iso-butanol, pentanol, hexanol and the like. The amounts of the salt of the carboxylic acid and the alcohol used are each equimolar amount stoichiometrically, relative to the compound of formula V. The reaction temperature is preferably from 50° to 200° C. The reaction is usually accomplished for 1 to 15 hours, followed by known isolation and purification procedures to give the final compound of formula I'.

Furthermore, the compound of Formula I wherein R' is a hydrogen atom can be easily obtained by hydrolyzing the compound of Formula I' according to the ordinary hydrolysis of esters using sodium hydroxide, potassium hydroxide and the like.

The compounds of the present invention have a potent protective effect against hepatotoxicity induced by carbon tetrachloride, thioacetoamide and the like when compared with the above prior art compounds, and are useful as the therapeutic agents for chronic hepatistis, hepatic cirrhosis and the lie. For the purposes, these compounds can be administered by oral route or by parenteral route such as intravenous, intramusclar, subcutaneous and percutanous route. The dosage forms of oral administration are tablets, pills, granules and the like, all of which are prepared by known methods. For example, pills are prepared using polyethyleneglycol and detergents, or using polyvinylpyrrolidone, polyvinylacetate, lemon oil and the like. The dosage forms of parenteral administration are injectional preparations, ointments and the like, all of which are prepared by ordinary manners.

The dose of the compound of the present invention depends on the compounds, administration route and severity of diseases, but usually it is in the range from 0.5 to 5 mg/kg/day.

The present invention will be illustrated in more detail in the following examples.

EXAMPLE 1

Preparation of 6-methoxycarbonyl-6'-hydroxymethyl-2,3,2',3'-bis(methylenedioxy)-4,4'-dimethoxybiphenyl (1) Preparation of 2,3,2',3'-bis(methylenedioxy)-4,4'-dimethoxybiphenyl-6,6'-dicarboxylic acid (III, R=CH₃):

A suspension of 8 g of dimethyl 4,4'-dimethoxy-5,6,5',6'-dimethylenedioxybiphenyl-2,2'-dicarboxylate (hereinafter referred to as "DDB") and 4 g of sodium hydroxide in a mixture of 105 ml of acetone and 70 ml of water was stirred under refluxing for 4 hours. After removal of acetone, the resulting alkaline solution was acidified with conc. hydrochloric acid. The precipitated white solid was filtered and washed with water to give 7.28 g (yield 98%) of the title dicarboxylic acid, m.p. 260° C.

(2) Preparation of 2,3,2',3'-bis(methylenedioxy)-4,4'-dimethoxybiphenyl-6,6'-dicarboxylic anhydride (IV, R=CH₃):

A suspension of 5 g of 2,3,2',3'-bis(methylenedioxy)-4,4'-dimethoxybiphenyl-6,6'-dicarboxylic acid obtained in the item (1) in 35 ml of acetic anhydride was refluxed with stirring for 4 hours. After evaporation of the solvent 30 ml of benzene was added to the residue, (3) Preparation of 2,3,2',3'-bis(methylenedioxy)-4,4'-dimethoxybiphenyl-6,6'-lactone (V, R=CH₃):

A suspension of 5 g of 2,3,2,3'-bis(methylenedioxy)-4,4'-dimethoxybiphenyl-6,6'-dicarboxylic anhydride obtained in the item (2) and 2 g of sodium borohydride in 150 ml of tetrahydrofuran was cooled in an ice-bath and stirred for 10 minutes. Then, the reaction mixture was refluxed for 4 hours, and the white solid which formed was separated. To the reaction mixture was added dropwise 6N hydrochloric acid, and the reaction mixture was filtered. After removal of the solvent, chloroform was added to the residue. The chloroform solution was washed four times with water, then dried over anhydrous sodium sulfate, and evaporated to give 5 g of a solid.

A solution of 2 g of the above solid and 1 g of p-toluenesulfonic acid in 100 ml of benzene was refluxed for 3 hours. The solution was washed twice with water, and the organic layer was dried over anhydrous sodium sulfate and evaporated to dryness to give 1.16 g (yield 63%) of the title compound as a white solid, m.p. 223°-225° C.

(4) Preparation of 6-methoxycarbonyl-6'-hydroxymethyl-2,3,2',3'-bis(methylenedioxy)-4,4'-dimethoxybiphenyl (I', R=CH$_3$):

A mixture of 0.5 g of 2,3,2',3'-bis(methylenedioxy)-4,4'-dimethoxybiphenyl-6,6'-lactone obtained in the item (3) and 0.8 g of anhydrous sodium acetate in 50 ml of methanol was refluxed for 7 hours After cooling, the precipitated crystal (0.24 g of unreacted 2,3,2',3'-bis(methylenedioxy)-4,4'-dimethoxybiphenyl-6,6'-lactone) was removed. The filtrate was evaporated to dryness, and the formed white solid was dissolved in water and extracted with chloroform. The organic layers were combined and dried over anhydrous sodium sulfate. Removal of the solvent gave 0.2 g of the title compound as a white crystalline solid, m.p. 137°-140° C.

IR(KBr)cm$^{-1}$ 3450, 2950, 1710, 1640, 930.

$^1$HNMR(CDCl$_3$)ppm 2.15(s, 1H), 3.79(s, 3H), 4.00(s, 3H), 4.02(s, 3H), 4.42(s, 2H), 6.00(s, 2H), 6.12(s, 2H), 6.84(s, 1H), 7.42(s, 1H).

In similar manner, the following compounds were obtained.

6-Ethoxycarbonyl-6'-hydroxymethyl-2,3,2',3'-bis(methylenedioxy)-4,4'-dimethoxybiphenyl, m.p. 84°-86° C., 6-n-Butoxycarbonyl-6'-hydroxymethyl-2,3,2',3'-bis(methylenedioxy)-4,4'-dimethoxybiphenyl, m.p. 80°-83° C., 6-Methoxycarbonyl-6'-hydroxymethyl-2,3,2',3'-bis(methylenedioxy)-4,4'-di-n-propoxybiphenyl, m.p. 115°-120° C.

EXAMPLE 2

Preparation of 6-carboxy-6'-hydroxymethyl-2,3,2',3-bis(methylenedioxy)-4,4'-dimethoxybiphenyl A solution 2.0 g of 6-methoxycarbonyl-6'-hydroxymethyl- 2,3,2',3'-bis(methylenedioxy)-4,4'-dimethoxybiphenyl obtained in Example 1 and 0.66 g of potassium hydroxide in 20 ml of acetone was refluxed for 3 hours. After evaporation of the acetone, the solution was acidified with conc. hydrochloric acid, and there was obtained a white precipitate, which was then filtered and washed with water to give 1.86 g of the title compound, m.p. 192°-195° C.

EXAMPLE 3

Preparation of Pills

To polyethyleneglycol (molecular weight 4000-6000) which was dissolved under heating were added 6-methoxycarbonyl-6'-hydroxymethyl-2,3,2',3'-bis(methylenedioxy)-4,4'-dimethoxybiphenyl and Tween-80, the mixture was stirred, and pills were prepared from the mixture using pill machine. The pills were thoroughly solidified by liquid parafin to give sugar coated pills.

EXPERIMENTS

Throughout the following experiments, male mice weighing 18-22 g were used, and unless otherwise indicated, the compound of the present invention [6-methoxycarbonyl-6'-hydroxymethyl-2,3,2',3'-bis(methylenedioxy)-4,4'-dimethoxybiphenyl (hereinafter referred to as "Compound 1")]]and DDB of a comparative drug are each suspended in 2% of Tween-80 before administered orally.

Effect on SGPT and SGOT levels in carbon tetrachloride-intoxicated mice (9 mice per group)

Each group consisted of nine mice. The treated groups of mice were given three doses of Compound 1 twice at an interval of 8 hours on the first day, while one group was given corresponding volume of 2% of Tween-80 as control. At 4 p.m. of the second day, all mice were given i.p. 10 ml/kg of 0.1% of carbon tetrachloride in peanut oil. After a 16 hour fasting, all mice were sacrificed by decapitation. Serum transaminase (SGPT, SGOT) levels were determined.

The results are shown in Table 1.

TABLE 1

| Group | | SGPT (u/dl ± SD) | SGOT (u/dl ± SD) |
|---|---|---|---|
| Control | | 3110 ± 50 | 2087 ± 131 |
| DDB | 50 mg/kg | 2701 ± 243 | 1922 ± 174 |
|  | 100 mg/kg | 2965 ± 221 | 2019 ± 130 |
|  | 200 mg/kg | 2303 ± 318* | 1700 ± 185 |
| Compound 1 | 50 mg/kg | 2523 ± 273 | 1826 ± 203 |
|  | 100 mg/kg | 2126 ± 371** | 1739 ± 192 |
|  | 200 mg/kg | 947 ± 236*** | 1362 ± 148** |

*$P < 0.05$
**$P < 0.01$
***$P < 0.001$

From Table 1 it is obvious that Compound 1 was effective in protection against carbon tetrachloride hepatotoxicity. Both SGPT and SGOT levels of mice treated with 200 mg/kg of Compound 1 significantly lowered as compared with the carbon tetrachloride control. The 100 mg/kg of Compound 1 markedly decreased SGPT level.

(B) Effect on SGPT, SGOT and liver triglyceride levels in acetaminophen-intoxicated mice Thirty six mice were divided equally into 4 groups. On the first day, one group was given 2% of Tween-80 as control, while other groups were each given two doses of Compound 1 at an interval of 8 hours. All mice were injected i.p. 110 mg/kg of acetaminophen 16 hours after the last administration of Compound 1. After fasting overnight, all mice were decapited. SGPT, SGOT and liver triglyceride levels were determined.

The results are shown in Table 2.

TABLE 2

| Group | | SGPT (u/dl ± SD) | SGOT (u/dl ± SD) | Liver triglyceride (mg/kg) |
|---|---|---|---|---|
| Control | | 1504 ± 330 | 1695 ± 390 | 57.4 ± 18.3 |
| DDB | 200 mg/mg | 1100 ± 660 | 1130 ± 651* | 56.2 ± 27.6 |
| Compound 1 | 100 mg/kg | 935 ± 660* | 1000 ± 651* | 52.0 ± 13.8 |
|  | 200 mg/kg | 550 ± 495*** | 565 ± 522*** | 50.0 ± 27.6 |

*$P < 0.05$
***$P < 0.001$

As shown in Table 2, Compound 1 (200 mg/kg, 100 mg/kg) was effective in lowering SGPT and SGOT levels elevated by acetaminophen. Compound 1 reduced liver triglyceride level elevated by acetaminophen. The liver lesions such as inflammation and necrosis of Compound 1-treated mice were ameliorated.

(C) Effect on mortality induced by acetaminophen in mice (14 mice per group)

Each group consisted of 14 mice. The procedure of the treatment was the same as mentioned in the item (B). All mice were given i.p. 400 mg/kg of acetaminophen 24 hours after the second dose of Compound 1. Survival numbers of mice were recorded within 5 days.

The results are shown in Table 3.

TABLE 3

| Group | Number | Number of survival | Mortality (%) |
|---|---|---|---|
| Control | 14 | 3 | 78 |
| Compound 1 (200 mg/kg) | 14 | 11 | 21 |

As indicated in Table 3, Compound 1 at the dose of 200 mg/kg significantly decreased the mortality of mice induced by acetaminophen.

(D) Effect on SGPT, SGOT and liver triglyceride levels in thioacetamide-intoxicated mice (9 mice per group)

Each group consisted of nine mice. The procedure of this experiment was just the same as mentioned in carbon tetrachloride-hepatotoxicity test. Only 50 mg/kg of thioacetamide was instead of carbon tetrachloride.

The results are shown in Table 4.

TABLE 4

| Group | | SGPT (u/dl ± SD) | SGOT (u/dl ± SD) | Lever triglyceride (mg/kg) |
|---|---|---|---|---|
| Control | | 2365 ± 1045 | 1174 ± 435 | 104 ± 35 |
| DDB | 200 mg/kg | 2035 ± 770 | 1217 ± 261 | 135 ± 46 |
| Compound 1 | 200 mg/kg | 1430 ± 550* | 565 ± 130*** | 115 ± 31 |

*P < 0.05
***P < 0.001

Table 4 showed that Compound 1 (200 mg/kg) was effective in lowering SGPT and SGOT levels elevated by thioacetamide.

(E) Effect on pentobarbital sleeping time in mice (10 mice per group)

Three groups of 10 mice were used in this experiment. One or 24 hours before the i.p. injection of sodium pentobarbital (50 mg/kg), 200 mg/kg of Compound 1 was given orally to the treated group of mice. The mice of control were given physiological saline. The interval between the lose and return of righting reflex of each mouse was recorded as sleeping time.

The results are shown in Table 5.

TABLE 5

| Group | | Sleeping time (min ± SD) | P value |
|---|---|---|---|
| Control | | 49 ± 22 | |
| DDB (200 mg/kg) | (24 hrs) | 23 ± 10 | <0.01 |
| | (1 hr) | 91 ± 57 | <0.05 |
| Compound 1 | (24 hrs) | 20 ± 8 | <0.001 |
| (200 mg/kg) | (1 hr) | 214 ± 85 | <0.001 |

As shown in Table 5, pentobarbital sleeping time significantly prolonged by a dose of 200 mg/kg of Compound 1 one hour before the injection of pentobarbital. When Compound 1 was administered 24 hours prior to the injection of pentobarbital, the sleeping time was markedly shortened. The data indicated indirectly that Compound 1 has inductive action on drug metabolism enzyme.

It was found that Compound 1 exhibited protective effect against hepatotoxicity induced by carbon tetrachloride thioacetamide and acetaminophen in mice. In addition, Compound 1 increases the activity of drug metabolism enzymes.

(F) Acute toxicity

Ten male kunming strain mice weighing 18–20 g were used, and starved overnight. Compound 1 was suspened in 0.2% CMC-Na, and 5 mice were given orally compound 1 in a dose of 3 g/20 ml/kg. The other 5 mice were given 6 g/20 ml/kg. No noticeable change of the behavior of the mice was observed within 48 hours, and no death occured within 2 weeks.

What is claimed is:

1. A bis (methylenedioxy)biphenyl compound represented by the formula

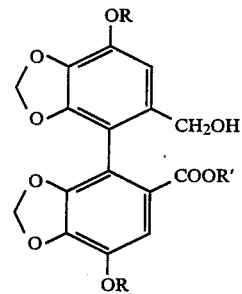

I wherein R is an alkyl group having 1 to 6 carbon atoms or a phenyl group, and R, is a hydrogen atom or an alkyl group having 1 to 6 carbon atoms.

2. A pharmaceutical composition for the treatment of liver diseases which comprises as an active ingredient a bis(methylenedioxy)biphenyl compound represented by the formula

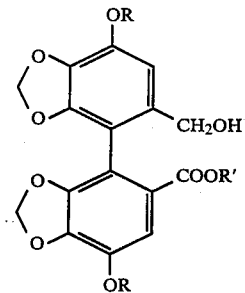

I wherein R is an alkyl group having 1 to 6 carbon atoms or a phenyl group, and R' is a hydrogen atom or an alkyl group having 1 to 6 carbon atoms, together with a pharmaceutically acceptable carrier or diluent.

* * * * *

UNITED STATES PATENT AND TRADEMARK OFFICE
CERTIFICATE OF CORRECTION

PATENT NO. : 4,868,207
DATED : September 19, 1989
INVENTOR(S) : Gu SHI-JIE

It is certified that error appears in the above—identified patent and that said Letters Patent is hereby corrected as shown below:

Column 4, line 15, "lie" should read --like--;

line 59, after "vent" insert a comma --,--;

line 59, after "residue," insert --and the mixture was filtered to give 4.4 g (yield 92%) of the title compound as a yellowish solid, m.p. 266°C.--; and line 62, "2,3,2,3'-bis(methylenedioxy)-" should read --2,3,2',3'-bis(methylenedioxy)- --.

Column 5, line 20, after "hours" insert a period --.--; and line 29, "3450" should read --3460--.

Column 6, line 10, "Compound 1")]]" should read --"Compound 1")]--;

line 13, before "Effect" insert --(A)--.

UNITED STATES PATENT AND TRADEMARK OFFICE
CERTIFICATE OF CORRECTION

PATENT NO. : 4,868,207

DATED : September 19, 1989

INVENTOR(S) : Gu SHI-JIE

It is certified that error appears in the above-identified patent and that said Letters Patent is hereby corrected as shown below:

Column 8, line 45, "R," should read --$R'$--.

Signed and Sealed this

Seventh Day of August, 1990

Attest:

HARRY F. MANBECK, JR.

*Attesting Officer*     *Commissioner of Patents and Trademarks*